United States Patent [19]

Stalcup et al.

[11] Patent Number: 5,693,048
[45] Date of Patent: Dec. 2, 1997

[54] INTRAMEDULLARY ROD GUIDE MEMBER LOCK

[75] Inventors: Gregory C. Stalcup, Columbia City; Rodney L. Bays, Pierceton; Billie W. McBroom, Milford, all of Ind.

[73] Assignee: Zimmer, Inc., Warsaw, Ind.

[21] Appl. No.: 403,036

[22] Filed: Mar. 13, 1995

[51] Int. Cl.⁶ .................................................. A61F 5/100
[52] U.S. Cl. ................................. 606/87; 606/86; 606/96
[58] Field of Search ................................ 606/86, 87, 88, 606/89, 96, 97, 98

[56] References Cited

U.S. PATENT DOCUMENTS

| | | | |
|---|---|---|---|
| 4,421,112 | 12/1983 | Mains et al. | 128/92 EB |
| 4,567,885 | 2/1986 | Androphy | 128/92 H |
| 4,703,751 | 11/1987 | Pohl | 128/92 VW |
| 4,738,254 | 4/1988 | Buechel et al. | 128/92 VW |
| 4,759,350 | 7/1988 | Dunn et al. | 128/92 VW |
| 4,791,919 | 12/1988 | Elloy et al. | 128/92 VW |
| 4,892,093 | 1/1990 | Zarnowski et al. | 606/82 |
| 4,952,213 | 8/1990 | Bowman et al. | 606/79 |
| 5,053,037 | 10/1991 | Lackey | 606/79 |
| 5,098,383 | 3/1992 | Hemmy et al. | 604/116 |
| 5,108,401 | 4/1992 | Insall et al. | 606/79 |
| 5,122,144 | 6/1992 | Bert et al. | 606/88 |
| 5,234,433 | 8/1993 | Bert et al. | 606/88 |
| 5,250,050 | 10/1993 | Poggie et al. | 606/79 |
| 5,364,401 | 11/1994 | Ferrante et al. | 606/84 |
| 5,484,446 | 1/1996 | Burke et al. | 606/87 |

FOREIGN PATENT DOCUMENTS

| | | |
|---|---|---|
| 0 104 732 | 4/1984 | European Pat. Off. . |
| 0 380 451 | 8/1990 | European Pat. Off. . |

*Primary Examiner*—Michael Powell Buiz
*Assistant Examiner*—Mark S. Leonardo
*Attorney, Agent, or Firm*—Todd A. Dawson

[57] ABSTRACT

The invention is directed to an intramedullary guide rod assembly for use in orthopaedic surgery for aligning one or more milling or cutting guides. A guide member is pivotally connected to an intramedullary guide rod intermediate the proximal and distal ends thereof. An alignment mechanism aligns the guide member to the intramedullary guide rod while a biased locking mechanism prevents alignment changes during application of impact forces.

10 Claims, 1 Drawing Sheet

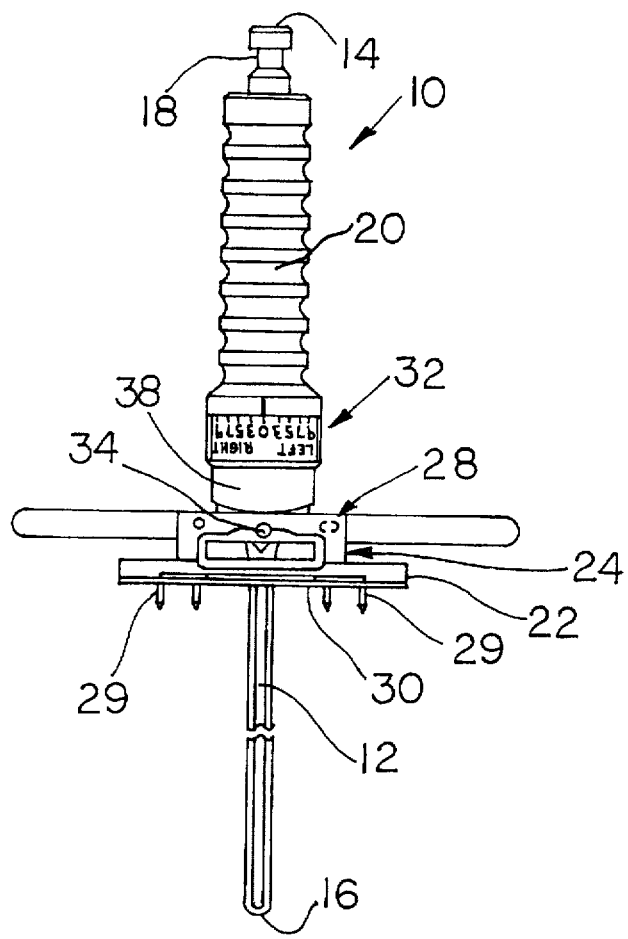
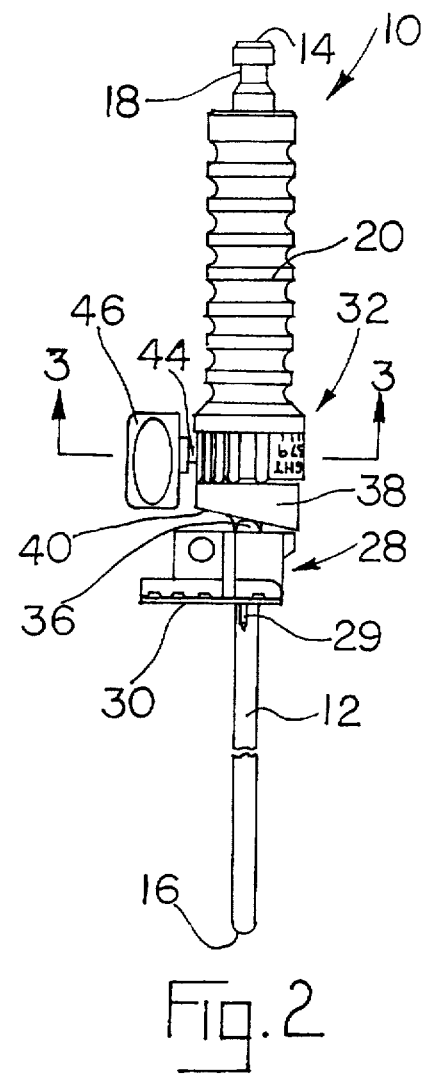
Fig. 1
Fig. 2
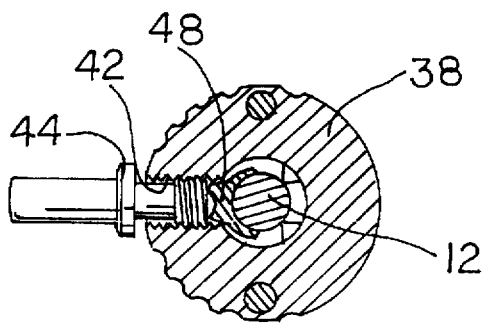
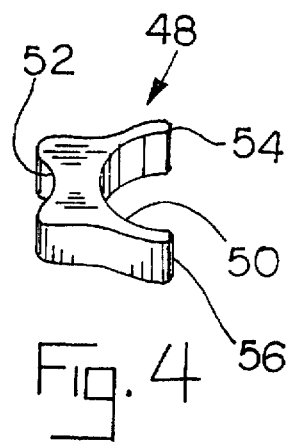
Fig. 3
Fig. 4

INTRAMEDULLARY ROD GUIDE MEMBER LOCK

BACKGROUND OF THE INVENTION

1. Field of the Invention

The present invention relates to instrumentation used in orthopaedic surgery, and, more particularly, to instrumentation providing for the alignment of milling guides and tools used to prepare bone for receiving a prosthesis.

2. Description of the Related Art

In an orthopaedic surgery to replace part or all of a patient's joint with a prosthetic implant, a portion of the bone is prepared to closely match the mating surfaces of the implant. During an orthopaedic surgery to replace a knee joint, the distal end of the femur is prepared to accommodate a femoral knee component and the proximal end of the tibia is prepared to accommodate a tibial component.

Depending on the type of implant to be accommodated by the femur, and the particular side of body with which the implant is to be mated, there is a small range of angles to which the implant must be oriented relative to the mechanical axis of the bone. Typically, in the preparation of the femur, for example, one or more cutting guides are placed adjacent the distal femur in a specific order to resect portions of the femur in succession. These cutting guides are generally individually aligned by the surgeon with reference to specific anatomic landmarks.

Prior intramedullary rods include alignable guide bases or members that are subjected to large amounts of vibrational force during the orthopedic procedure. During the procedure, the apparatus is normally hit with a hammer and utilized as a guide for power tools for cutting or shaping bone. The forces induced by vibration through the intramedullary rod at times may change the pre-set angle between the guide base and intramedullary rod, thereby altering the proper alignment for subsequent milling or cutting guides and tools.

What is needed in the art is an instrument, particularly an intramedullary rod, with an attached guide mechanism that is able to withstand the vibration created by a hammer or powered tools.

SUMMARY OF THE INVENTION

The present invention provides an intramedullary rod assembly with a guide mechanism that aligns the guide base and other instruments to the bone receiving a prosthesis. The intramedullary rod assembly includes a lock mechanism to lock the alignment mechanism between the intramedullary rod and guide member.

The invention additionally includes a resilient yoke spring that releasably locks the adjustment mechanism to the intramedullary rod. The resilient yoke acts as a biasing mechanism to spring load a screw utilized to lock the adjustment mechanism thereby preventing rotation of the screw when the intramedullary rod is subjected to vibratory forces.

An advantage of the intramedullary guide rod assembly of the present invention is that any shock or vibration through the guide rod assembly is damped by the resilient yoke so that the thumb screw lock mechanism does not rotate backward or back off and separate from the intramedullary rod. The yoke damps the external vibratory forces applied to the screw through the guide assembly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a front elevational view of one embodiment of the intramedullary rod of the present invention;

FIG. 2 is a side elevational view of the intramedullary rod shown in FIG. 1;

FIG. 3 is a sectional view of the intramedullary rod of FIG. 2, taken along line 3—3 and viewed in the direction of the arrows; and FIG. 4 is a perspective view of the yoke or stop of FIG. 3.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings and particularly FIG. 1, an embodiment of an intramedullary guide rod assembly 10 of the present invention is shown. In general, intramedullary guide rod assembly 10 includes an intramedullary guide rod 12 having a proximal end 14 and a distal end 16. Proximal end 14 includes a fitting or portion 18 for accommodating a gripping device for the removal of the intramedullary guide rod assembly 10 from a bone, such as the femur. A ridged handle 20 may be integrally formed or attached about the proximal portion of intramedullary rod 12 to assist the surgeon in manually gripping rod 12. During an orthopedic operation, proximal end 14 is normally hit with a hammer to drive the intramedullary rod assembly 10 into the bone.

Guide member or base 28, utilized for aligning milling and cutting guides to a bone, is located and pivotally attached to intramedullary rod 12 at a location which is intermediate proximal end 14 and distal end 16. A platform 22 is attached by a pair of legs 24 extending therefrom as illustrated in FIG. 1, and secured to a base 28. Platform 22 includes a spacer 30 which may be selectively attached to platform 22 by fasteners. Platform 22 and spacer 30 of guide member 28 both include central openings for accommodating intramedullary rod 12 therethrough. Spacer 30 or platform 22 may include extending pins 29 so that base 28 may be temporarily fixed to a bone and utilized for establishing a reference point relative to the bone to be milled or cut.

For further details of the milling and cutting alignment guides attachable to guide base 28, and use of an intramedullary rod, reference is made to co-pending U.S. patent application Ser. No. 08/169,459, which is assigned to the assignee of the present hereby expressly incorporated herein by reference.

As depicted, the figure guide base 28 is pivotally connected to intramedullary rod 12 by pivot 34. Pivot 34 would permit a wide continuum of relative angular positions between guide base 28 and intramedullary rod 12 if it were not for alignment mechanism 32.

Alignment mechanism 32, in one form of the present invention, is utilized for fixating and determining the relative angular position between guide base 28 and intramedullary rod 12, and is most clearly shown in FIGS. 1 and 2. Alignment mechanism 32 includes an engagement member such as at least two ball bearing members 36 connected to guide base 28 and oriented opposite cam 38. Rotatable cam 38 is disposed about intramedullary rod 12 having a beveled bottom surface 40 as shown in FIG. 2. The operation and construction of alignment mechanism 32 is more fully described in co-pending U.S. patent application Ser. No. 08/265,884, filed Jun. 27, 1994, now U.S. Pat. No. 5,484,446, entitled, Alignment Guide for use in Orthopaedic Surgery, which is assigned to the assignee of the present invention and hereby expressly incorporated herein by reference.

The present invention, in one form thereof, comprises a locking mechanism to prevent rotation of cam 38 about intramedullary rod 12 which would thereby cause a change in the relative angle of guide member 28. As shown in FIG. 3, cam 38 includes a threaded bore 42 transverse to intramedullary rod 12. Threaded bore 42 is interfit with a threaded stud 44 that may be attached to a knob or thumb wheel 46 as shown in FIG. 2.

To prevent rotation of cam 38 about intramedullary rod 12, stud 44 is manually rotated through bore 42 into engagement with intramedullary rod 12. This engagement would normally prevent rotation of cam 38 about rod 12. However, during orthopedic procedures, impact forces and other forces may be applied through the intramedullary rod assembly 10 via a hammer or powered instrument. To ensure stud 44 does not back off and allow cam 38 to rotate during application of such forces, a resilient yoke or stop 48 is disposed between intramedullary rod 12 and stud 44. Resilient yoke 48, more clearly shown in FIG. 4, includes a first side 50 shaped to substantially accommodate intramedullary rod 12 and on opposite side 52 shaped to accommodate an end of stud 44. Although first side 50 is shaped to have two opposite extending side arms 54 and 56 the particular shape of and distance between arms 54 and 56 are such that when yoke 48 is forcibly compressed by stud 44 against intramedullary rod 12, the compression causes arms 54 and 56 to flex and spread apart. One structure that would create such an effect would be if first side 50 would have a smaller radius of curvature than that of the location it engages on intramedullary rod 12. This action causes a biasing force to be created between intramedullary rod 12 and stud 44 which thereby prevents reverse rotation and backing out of stud 44 through threaded bore 42 upon occurrence of vibration of intramedullary guide rod assembly 10, either through forces acting upon intramedullary rod 12 or guide base 28.

Although resilient yoke 48 includes two side arms 54 and 46 to form a biasing structure, the concept of including a resilient member acting with stud 44 is not thereby limited. Other shapes and forms of yoke 48 may be utilized equivalently as long as the function of damping shock or vibrations forces is accomplished to prevent backing out or loosening of stud 44 relative bore 42.

The physical properties of the material utilized in resilient yoke 48 include any type of spring-type material that undergoes substantially elastic deformation and maintains such elastic deformation under all operating conditions of intramedullary guide rod assembly 10. In the preferred embodiment, yoke 48 is constructed from stainless steel. Alternatively, other types of structures may be utilized to accomplish the damping function of resilient yoke 48, such as known damping structures including non-compressible fluids, composites, plastics and resilient bearings.

In operation, alignment means 32 of the present invention enables a surgeon to select particular angular positions between guide base 28 and intramedullary rod 12. The method of locking guide base 28 to a predetermined position relative to rod 12 requires cam 38 to become temporary unlocked and disengaged, while cam 38 is rotated about pivot 34, causing guide base 28 to pivot relative to the intramedullary rod.

More particularly, the surgeon first rotates stud 44 through bore 42 by rotating knob 46, thereby releasing yoke 48 from intramedullary rod 12. As cam 38 is then rotated, a change of force on ball bearings 36 (due to the angled bottom surface 40 of cam 38) causes guide base 28 to pivot to a new position. After guide base 28 has been pivoted to the new, desired position, knob 46 is rotated to cause stud 44 to bias yoke 48 into rod 12. Rotation of stud 44 toward rod 12 and the subsequent increase of the bias force between stud 44 and rod 12 prevents rotation of cam 38 about rod 12 and thereby locks the position of guide base 28 to intramedullary rod 12.

Yoke 48, interposed between rod 12 and stud 44, substantially prevents vibrations from being transferred from rod 12 to stud 44 that could possibly induce rotation of stud 44 in a reverse rotation and permit relative rotational movement between cam 38 and intramedullary rod 12. Utilization of resilient yoke 48 thereby locks guide base 28 in its pre-selected position relative to intramedullary rod 12.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An intramedullary guide assembly, comprising:
    an intramedullary guide rod, said guide rod having a proximal end and a distal end;
    a guide member pivotally connected to said guide rod and located intermediate said proximal end and said distal end;
    an alignment means aligning said guide member relative to said guide rod;
    locking means for locking said guide member relative to said guide rod; and
    means, interposed between said guide rod, said alignment means and said locking means, for damping vibrations between said guide rod, said alignment means and said locking means, thereby ensuring said locking of said guide member relative to said guide rod.

2. The guide rod of claim 1 in which said alignment means comprises a cam rotatably connected to said guide rod, and an engagement member on said guide member, whereby rotation of said cam causes pivotal movement of said engagement member relative said guide rod.

3. The guide rod of claim 1 in which said locking means engages said guide rod for preventing movement between said guide rod and said guide member.

4. The guide rod of claim 1 in which said damping means is a resilient member.

5. The guide rod of claim 4 in which said resilient member includes two legs oriented on opposite sides of said guide rod.

6. The guide rod of claim 1 in which said guide member is configured for temporary fixation to a bone.

7. An intramedullary guide rod assembly, comprising:
    an intramedullary guide rod, said rod having a proximal end and a distal end;

a guide member pivotally connected to said guide rod and located intermediate said proximal end and said distal end;

an alignment means for aligning said guide member to said guide rod relative to said rod axis; and a locking mechanism comprising a stud threadingly engaging through said alignment means for locking said guide member relative to said guide rod, said locking mechanism including a resilient member disposed between said stud and said guide rod so that vibrations through said guide rod assembly are damped and prevented from reverse rotating said stud and thereby unlocking said guide member relative to said guide rod.

8. The guide rod of claim 7 in which said resilient member includes two legs oriented on opposite sides of said guide rod.

9. The guide rod of claim 7 in which said resilient member is formed of stainless steel.

10. An orthopaedic instrument comprising first and second members held in a fixed relation to one another by a lock means extending through the first member in engagement against the second member, the lock means including a clamping means in contact with the first member for clamping vibrations between the first member and the lock means, wherein said lock means includes a screw member threadibly carried by the second member and having first and second ends, said clamping means includes a resilient yoke positioned between the first member and the second end of the screw member.

* * * * *